(12) United States Patent  
Pakhomov et al.

(10) Patent No.: US 8,139,339 B2
(45) Date of Patent: Mar. 20, 2012

(54) MODULATION OF NEUROMUSCULAR FUNCTIONS WITH ULTRASHORT ELECTRICAL PULSES

(75) Inventors: Andrei Pakhomov, Norfolk, VA (US); Karl Schoenbach, Norfolk, VA (US); Juergen Kolb, Norfolk, VA (US); Ravindra Joshi, Virginia Beach, VA (US)

(73) Assignee: Old Dominion University Research Foundation, Norfolk, VA (US)

( * ) Notice: Subject to any disclaimer, the term of this patent is extended or adjusted under 35 U.S.C. 154(b) by 1006 days.

(21) Appl. No.: 12/050,009

(22) Filed: Mar. 17, 2008

(65) Prior Publication Data

US 2008/0228244 A1    Sep. 18, 2008

Related U.S. Application Data

(60) Provisional application No. 60/895,187, filed on Mar. 16, 2007.

(51) Int. Cl.
*F41B 15/04* (2006.01)
*H01T 23/00* (2006.01)

(52) U.S. Cl. ........................................................ 361/232
(58) Field of Classification Search .................... 361/232
See application file for complete search history.

(56) References Cited

U.S. PATENT DOCUMENTS

| | | | |
|---|---|---|---|
| 6,636,412 B2 * | 10/2003 | Smith | 361/232 |
| 2006/0269531 A1 * | 11/2006 | Beebe et al. | 424/93.21 |
| 2007/0093870 A1 * | 4/2007 | Maschino | 607/2 |
| 2008/0228244 A1 * | 9/2008 | Pakhomov et al. | 607/72 |
| 2008/0294221 A1 * | 11/2008 | Kilgore et al. | 607/46 |
| 2009/0210041 A1 * | 8/2009 | Kim et al. | 607/117 |
| 2010/0298825 A1 * | 11/2010 | Slizynski et al. | 606/41 |

\* cited by examiner

*Primary Examiner* — Ronald W Leja
(74) *Attorney, Agent, or Firm* — Novak Druce + Quigg LLP

(57) ABSTRACT

A system for producing maximal, but reversible bioeffects, for neuromuscular disruption. Methods for facilitation of neuromuscular functions in diseases and conditions of decreased excitability are provided.

8 Claims, 7 Drawing Sheets

MODULATION OF NEUROMUSCULAR FUNCTIONS WITH ULTRASHORT ELECTRICAL PULSES

RELATED APPLICATION

This application claims the benefit of U.S. Provisional Application No. 60/895,187, which was filed Mar. 16, 2007 and which is incorporated herein in its entirety.

STATEMENT REGARDING FEDERALLY SPONSORED RESEARCH OR DEVELOPMENT

The invention was made with U.S. government support under US Air Force Contract Number F41624-01-C-7002 awarded by the Joint Non-Lethal Weapons Directorate. The U.S. government has certain rights in the invention.

FIELD OF THE INVENTION

The invention is related to neuromuscular modulation (facilitation or inhibition) by pulsed electric fields.

BACKGROUND

Experimental studies on single cells have shown that application of pulsed voltages, with pulse duration of 300 ns and an electric field on the order of 10 kV/cm, cause sudden alterations in the intracellular free calcium concentration, followed by immobilization ("stunning") of the cell (E. S. Buescher and K. H. Schoenbach, "The Effects of Submicrosecond, High Intensity Pulsed Electric Fields on Living Cells—Intracellular Electromanipulation," *IEEE Trans. on Dielectrics and Electrical Insulation* 10, 788-794 (2003)). The duration of immobilization, which can range from a few seconds to tens of minutes, is dependent on the amplitude of the applied voltage, but also on the pulse duration. For aquatic organisms, the optimum pulse duration for stunning was found to be approximately 300 ns (A. Ghazala and K. H. Schoenbach, "Biofouling Prevention with Pulsed Electric Fields," *IEEE Trans. Plasma Science* 28, 115-121 (2000)).

There is a need in the art to obtain maximal, but reversible bioeffects, for neuromuscular disruption. Likewise, there is a need for facilitation of neuromuscular functions in diseases and conditions of decreased excitability.

SUMMARY

A system for producing maximal, but reversible bioeffects, for neuromuscular disruption is provided. Methods for facilitation of neuromuscular functions in diseases and conditions of decreased excitability are also provided.

In one embodiment, a pulse generator comprises a pulse-forming network and a closing switch. Preferably, the pulse-forming network is arranged in a Blumlein configuration or a transmission line configuration.

In another embodiment, the pulse generator comprises at least two generators, each of which generates electric fields up to 10 MV/cm and a pulse duration of about 1 picosecond up to 1 sec, at a voltage of less than or equal to 1 MV. Preferably, the at least two generators each generate fields of different pulse, amplitude, frequency and number.

In another embodiment, the closing switch allows switching up to 100 kV, 10 000 amps and rise times up to 900 nanosecond (ns).

In another embodiment, the pulse generator generates electric fields up to 10 MV/cm. Preferably, the pulse generator generates electric fields of 10 kV/cm to 1000 kV/cm.

In another embodiment, the pulse generator that generates a pulse duration of about 1 picosecond up to 1 sec. and a voltage of less than or equal to 1 MV.

In another embodiment, the pulse generator is connected by two electrical cables with the tissue, or, a pulse generator, which charges a capacitor or a pulse-forming network to high voltage, which is then transferred to the tissue. The poles of the capacitor or pulse-forming network are connected with two cables with the tissue.

In another embodiment, the pulse generator generates electric fields of up to 500 kV/cm in tissue between the contacts of the cable at/in the tissue. In another aspect, the pulse generator charges a capacitor or pulse forming network, which, connected to the tissue, generates electric fields up to 500 kV/cm in tissue between the two contacts.

In another embodiment, the pulse generator or the charged capacitor and pulse-forming network, respectively, generates an electrical pulse with pulse duration of about 10 picosecond up to 110 microseconds and a voltage of less than or equal to 100 kV.

Another embodiment is a method of incapacitating a mammal. The method comprises aiming a pulse generator at the mammal; subjecting the cells or tissues to an electric field generated by a pulse generator, a pulse-forming network, and a closing switch; and, incapacitating the mammal.

In another embodiment, the pulse generator generates electric field pulses of up to 1 second and a voltage of less than or equal to 1 MV.

In another embodiment, the mammal is incapacitated using at least two pulse generators wherein each generates fields of different pulse, amplitude, frequency and number. The pulse generators each can have a pulse duration which is fixed to one value.

In another embodiment, a method of facilitating neuromuscular responses in treatment of neuromuscular diseases and conditions associated with decreased excitability in the efferent pathway from cerebral neurons to peripheral muscles comprises applying a pulse generator which charges a capacitor or pulse forming network, which, connected to the tissue generates electric fields up to 500 k/cm in tissue between the two contacts.

In another embodiment, a method of blocking nerve conduction comprises applying a pulse generator which charges a capacitor or pulse forming network, which, connected to the tissue, generates electric fields up to 500 kV/cm in tissue between the two contacts; permeabilizing the membrane by decreasing local input resistance; and, blocking nerve conduction.

In another embodiment, a method of blocking nerve conduction comprises applying a pulse generator which charges a capacitor or pulse forming network, which, connected to the tissue, generates electric fields up to 500 kV/cm in tissue between the two contacts; disrupting ion channels and inhibiting the ion channels; and, blocking nerve conduction. In some aspects, the ion channel is a voltage gated $Na^+$ channel.

In another embodiment, a method of facilitating neuromuscular responses in treatment of neuromuscular diseases and conditions associated with decreased excitability in the efferent pathway from cerebral neurons to peripheral muscles comprises incapacitating an animal or a person; subjecting the cells or tissues of the animal or person to an electric field generated by a pulse generator; and, incapacitating the animal or person.

BRIEF DESCRIPTION OF THE DRAWINGS

The advantages of this invention may be better understood by referring to the following description taken in conjunction with the accompanying drawings, in which:

FIG. 4A: nanosecond pulse generator; FIG. 4B: TASER simulator; FIG. 4C comparison of TASER simulator pulse with X26 TASER pulse. Note the different time scales.

FIG. 7B-TASER imitator). The onset for delayed inhibition is more a factor of two less in energy for 600 ns pulse compared to microsecond pulse.

FIG. 8A is an illustration of the experiment protocol: a 2-sec train of 4 stimuli (lower trace) applied to the sensorimotor cortex elicited 4 hindlimb twitches (upper trace). This stimulation was repeated every 10 sec; the initial 4 sec were recorded and the next 6 sec were not (time breaks are shown by vertical dashed lines). The arrow shows application of a high-voltage pulse. FIGS. 8B and 8C show examples of prolonged incapacitation in two different animals, induced by 4- and 6-A pulses, respectively. Cortex stimulation (not shown) was continued unchanged throughout the experiment, but failed to elicit hindlimb twitches for an extended period of time after the HV pulse ("prolonged incapacitation"). The inset shows the waveforms (current) for experiments in FIGS. 8B and 8C.

DETAILED DESCRIPTION

The invention provides a system for generating electrical pulses used for the incapacitation of mammals. The pulse generator can be arranged in a pulse-forming network in various configurations such as for example, a Blumlein configuration or a transmission line configuration. The pulse generator can also be configured to comprise a series of generators wherein each generates fields of different pulse, amplitude, frequency and number.

Application of pulsed voltages, with submicrosecond pulse duration and an electric field on the order of 10 kV/cm, to cells causes sudden alterations in the intracellular free calcium concentration, followed by immobilization of the cell. In order to examine electrical stimulation and incapacitation with such ultrashort pulses, experiments on anesthetized rats have been performed. The effect of single, 450 nanosecond monopolar pulses have been compared with that of single pulses with multi-microsecond duration (TASER pulses). Two conditions were explored: 1. the ability to elicit a muscle twitch, and, 2. the ability to suppress voluntary movement by using nanosecond pulses. The second condition is relevant for neuromuscular incapacitation. The results indicate that for stimulation microsecond pulses are advantageous over nanosecond pulses, whereas for incapacitation, the opposite seems to apply. The stimulation effects were seen to scale with electrical charge, whereas the disruption effects do not follow a simple scaling law. The increase in intensity (time of incapacitation) for a given pulse duration, is increasing with electrical energy, but is more efficient for nanosecond than for microsecond pulses. This indicates different cellular mechanisms for incapacitation, most likely subcellular processes, which have been shown to become increasingly important when the pulse duration is shortened into the nanosecond range. The consequences of reduced pulse duration are a reduction in weight and volume of the pulse delivery system, and likely, because of the lower required energy for neuromuscular incapacitation, reduced safety risks.

With ultrashort pulses, relatively high voltages are used, but the energy deposited per pulse is rather small, typically on the order of a Joule. Using pulse trains can further reduce the total energy applied while still retaining effectiveness. Thermal effects typically do not play a role in the bioeffects associated with ultrashort pulses.

Figure 2:
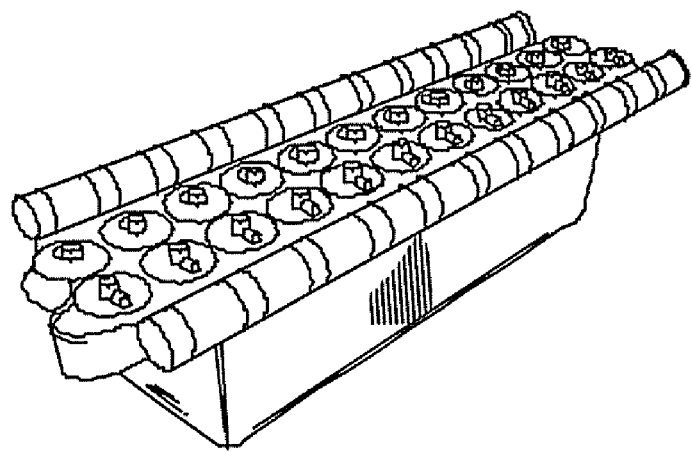
FIG. 2 is a scan of a photograph showing a Pulse Forming Network for the 300 ns pulse generator.

Experiments to optimize the stunning effect use a custom-built ns pulse generators, which can deliver rectangular pulses of well defined duration and amplitude to the target. Details of a pulse generator that can deliver rectangular voltage pulses of 300 ns and amplitudes of more than 40 kV are shown in FIG. 2. Such generators allow pulse amplitude, frequency, and number to be varied. Pulse duration is fixed for each generator to one value. Thus, varying the duration requires one generator for each pulse duration. Two sets of three pulse duration generators: 20 ns, 120 ns, and 600 ns can be used. These generators operate as transmission line generators. The voltage amplitudes are varied up to 20 kV, the repetition rates up to 10 Hz.

In vivo studies to determine the optimum electrical and pulse delivery conditions for neuromuscular incapacitation have been performed. Parameters are duration, amplitude, number, and frequency of the pulses. The animal studies were performed in male Sprague-Dawley rats. Cortex is stimulated via a constant current optical insulation unit. Electrical pulses of sub-ms duration, 0.5-2 mA are applied. With this system, hindpaw twitches in the contralateral limb are elicited. Twitches are continually recorded using an isotonic force transducer and BIOPAC data acquisition system. A single HV pulse (Taser™ or ns) or a train of HV pulses is applied to a selected body location after the first stimulus to the brain. The endpoint is the amplitude of current (and related charge transfer and energy) required to suppress "voluntary" twitches. Regardless of the mechanism, the lack of response to the cortical stimulus will clearly indicate incapacitation of the limb by HV pulses, and is used as a criterion to compare pulse efficacy. Testing of suppression efficacy is conducted with varying degrees of skin penetration and positions (spatial) of electrodes.

In Vitro Studies: Electrophysiology analyze HV effects on cell plasma membrane, conduction of excitation by nerve fibers, and the function of neuronal circuitry of the spinal cord also have been performed. In freshly isolated individual neurons and/or cultured neuron-like cells (e.g., GH3), HV effects on transmembrane currents and function of ion channels are explored by a whole-cell patch clamp technique. Different types of channels are selected by modifying intra- and extra-cellular ionic environment, by applying different stimulation/holding potential paradigms, and by using specific conduction blockers. HV effect on nerve conduction is studied in isolated sciatic nerve using classic approaches (extracellular recording). The ability of TASER™ and ns-duration HV pulses to reach the threshold depolarization and elicit action potentials in different types of nerve fibers is identified. Transverse live slices of the spinal cord are employed to analyze signal transduction between neurons in the reflex pathway using extracellular recording and patch clamp techniques. Pipette positioning in slices is performed using differential interference contrast infrared microscopy. Dorsal and ventral root potentials evoked by peripheral nerve(s) stimulation, analyze miniature potentials and evoked postsynaptic potentials in motor neurons are analyzed.

Calcium and Neurotransmitter Release: Immobilization of cells is related to calcium release. Based on effects of nsPEFs on cell membranes, it is highly likely that calcium mobilization in excitable cells will ensue through voltage-gated, plasma membrane channels that are coupled to neurotransmitter release. It is hypothesized that nsPEFs can recruit neurotransmitter release from nerve terminals at the neuronal synapses and neuromuscular junctions. Some experiments are designed to investigate mechanisms that control calcium mobilization from intracellular and extracellular sources, regulate neurotransmitter release, and modulate neuromuscular behavior in excitable (neuronal) cells and tissues. Firstly, define nsPEF conditions (duration, electric field, frequency) that promote or inhibit calcium mobilization and neurotransmitter release in cultured neurons in real time using fluorescent microscopy. This provides an understanding of the relationship between nsPEFs conditions and effects on physiological functions that relate to behavior control.

In Vivo Studies: Optimize pulse parameters, safety relative to skeletal muscle, cardiac and respiratory function. Animals used were Yucatan miniature swine weighing less than 50 Kg. As performed in the rat, incapacitation efficiency are evaluated from the degree of suppression of a hind leg twitch by different modalities of HV pulses discharged from generators. The hind leg twitches are initiated by low-current stimulation of the sensorimotor cortex as described above for rats. Contractions are recorded using an isotonic force transducer and BIOPAC data acquisition system. Efficacy is evaluated by the period of time to recovery of initial motor function and final recovery to full strength of contraction. Anesthetized animals are continuously monitored for EKG, respiration rate and volume, and body temperature. At selected times after stimulation with HV pulses, venous blood samples are collected from an indwelling catheter. Plasma concentrations of markers for cardiac and skeletal muscle stress or injury are measured using the I-STAT System (Abbott Labs). These include myoglobin, troponin I, lactate, bicarbonate, blood pH and $pCO_2$, interleukin-6, and Creatinine Kinase-MB. Comparisons can be made to samples drawn and prepared prior to any stimulation of the animal.

After collection of the data, the animal is euthanized with an overdose of barbiturate. A full necropsy is performed and tissue from the heart (SA and AV nodes), tissue directly beneath the stimulating electrodes, and tissue 2 and 5 cm from the electrodes is collected and prepared for histological examination by a veterinary pathologist. Physiologic data and results of the plasma markers was compared statistically upon completion of the study.

EXAMPLES

Example 1

Pulse Generators

Figure 1:
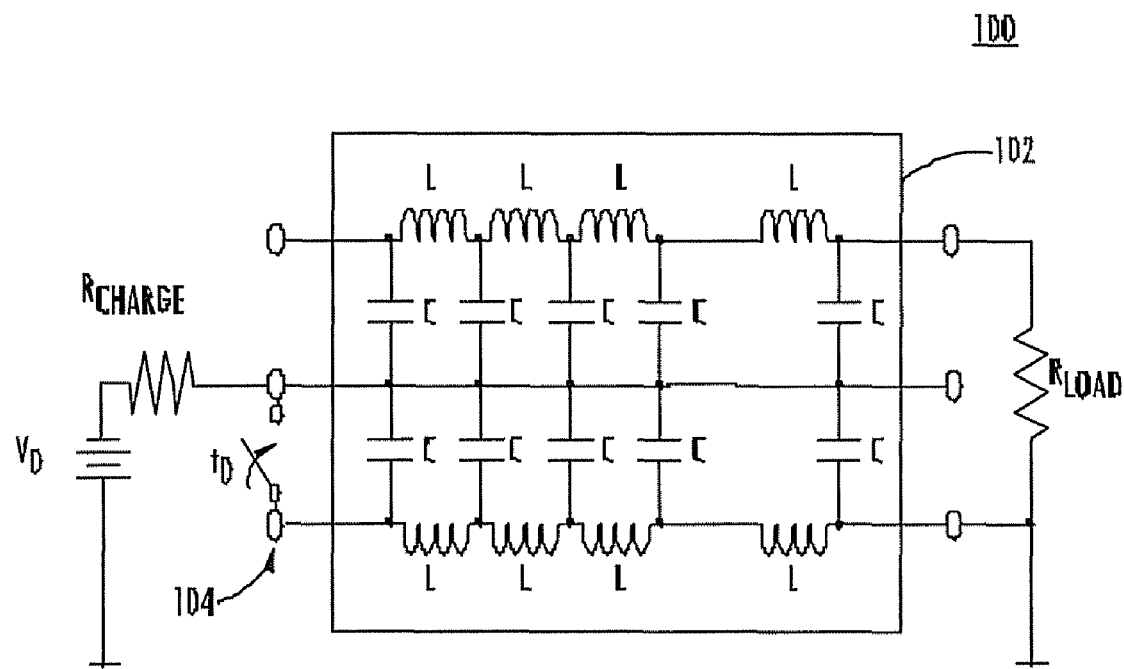
FIG. 1 is a schematic view of the equivalent circuit of a pulse generator, arranged in a Blumlein configuration.

Based on the previous experimental results (A. Ghazala and K. H. Schoenbach, *IEEE Trans. Plasma Science* 28, 115-121 (2000)), a pulse generator that can deliver rectangular voltage pulses of 300 ns and amplitudes of more than 40 kV to the test animal was developed. The pulse generator 100 is schematically illustrated in FIG. 1. The main components of such a system are the pulse-forming network 102, which determines the shape of the pulse, and a closing switch 104. A thyratron can be used as the closing switch 104, which allows switching of up to 40 kV and 1000 A, with a risetime of 30 ns. The pulse-forming network 102, an LC (inductance/capacitance) network, illustratively comprises a plurality of inductors, L, and capacitors, as shown in FIG. 1. It is arranged in a Blumlein configuration with an impedance of 250Ω. The capacitors have values of 200 pF and are designed to hold a voltage of up to 30 kV.

Figure 3:
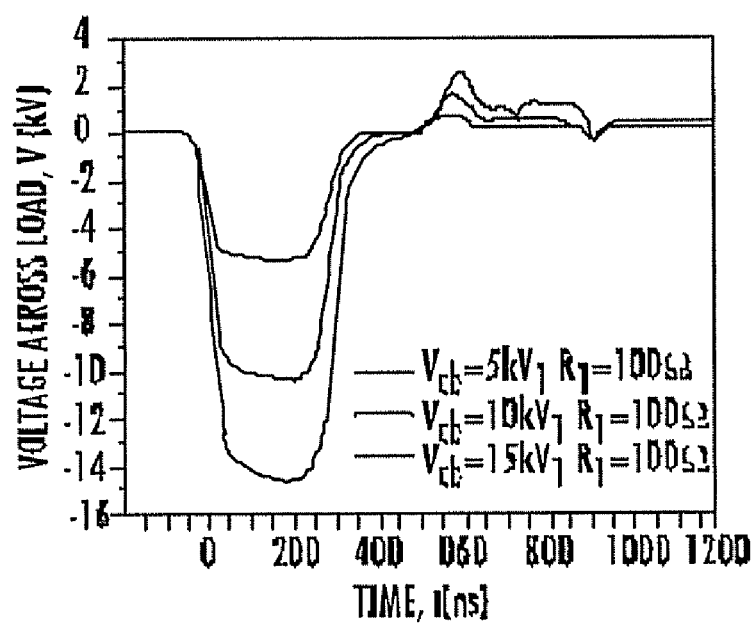
FIG. 3 is a graph showing Measured pulse shapes for 300 ns Blumlein pulse generator.

The arrangement shown in FIGS. 1-3 allows the generation of voltage pulses with an amplitude equal to the applied voltage, however charging of the Pulse Forming Network occurs through the load; in the case of animal experiments, through the animal. This can be avoided by arranging the Pulse Forming Network in a transmission line configuration. In this case, the pulse duration defined by the network changes to twice that of the Blumlein network, to 600 ns, and the pulse voltage is only half of the applied voltage. A review of nanosecond pulse generators for bioelectric applications can be found in. F. Kolb, S. Kono, and K. H. Schoenbach, "Nanosecond Pulsed Electric Field Generators for the Study of Subcellular Effects," *Bioelectromagnetics J.*, 27 (2006), incorporated herein by reference in its entirety.

Figure 4A:
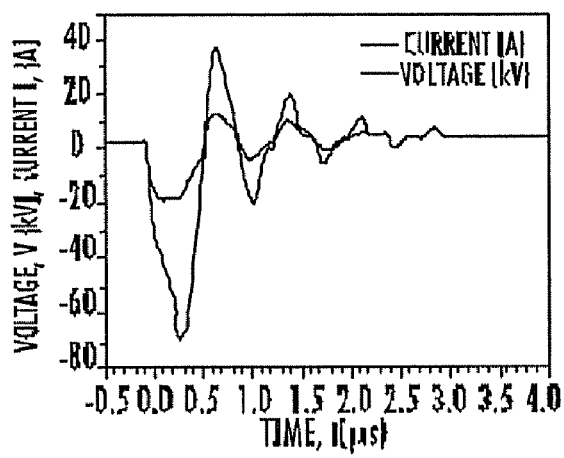
FIGS. 4A-4C are graphs showing voltage and current traces.
Figure 4B:
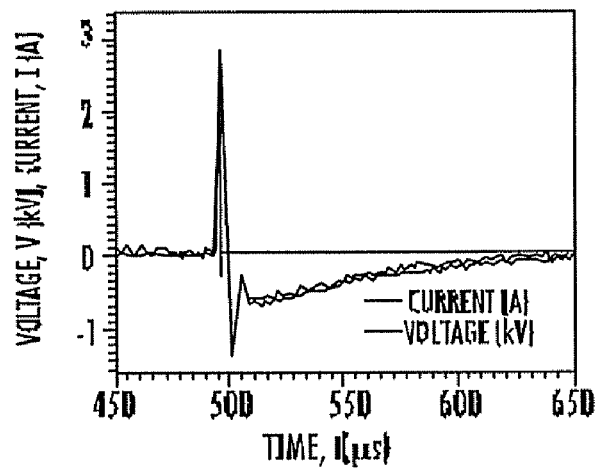
Figure 4C:
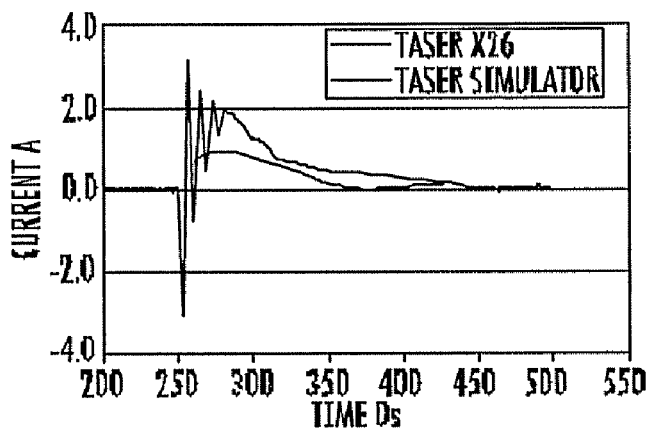

For the studies described in the following, the pulse-forming network was arranged in a transmission line configuration. The pulse duration (full width at half maximum) was in the range from 400 to 600 ns. Voltage and current traces are shown in FIG. 4A. A TASER® X26 model stimulator has been used as a baseline of comparison in the study. A pulser with similar pulse characteristics as the TASER® X26 was built by AIES. It has a similar pulse shape and timing with voltage variations made possible. The simulator wave shape is shown in the center. A comparison with a TASER X26 pulse is shown in FIG. 4C right.

Example 2

Stimulation Studies

A first set of experiments was performed with the goal of comparing the efficiency of Taser vs. ns pulses by their ability to elicit a muscle twitch. In short, an active electrode was inserted into the gastrocnemius muscle of an anesthetized rat; and the ground electrode was positioned over the skin, closer to the paw of the same extremity. Next, the voltage of the pulses was increased until a muscle twitch was detected. The threshold voltage and the corresponding charge transfer were the measures used to compare the efficiency of the two stimulation modalities.

Methods: The experiments have been performed on Sprague-Dawley rats purchased from Charles River Laboratories (Wilmington, Mass.) in groups of 5-6. Upon arrival, 1 rat was randomly removed for quality control testing that included microscopic examinations and necropsies. A 10-day quarantine was enforced. The animal on which the effect of electrical pulses was explored was anesthetized with Isoflurane and analgesia has been given I.M. as Xylazine 1 3 mg/kg. It was then placed in a sling with a thermal blanket. An isometric force transducer has been attached to the hind limb of interest at the ankle, as well as the grounding strap. Electrode gel was used to decrease skin impedances at the strap. The electrode consists of the barb electrode from the Taser International's X26 TASER® cartridge. The electrode was inserted so that the barb is just beneath the skin. The animal was exposed to a TASER® pulse, and the transducer force response was recorded. The voltage of the nanosecond pulser was then increased or decreased until the threshold for twitching was determined. This has been done by crossing over the pull force similar to the TASER® induced pull force three times. The threshold has been considered the average of three such crossings.

Results: The results of this study showed that the threshold for twitching was similar for nanosecond pulses and TASER simulator pulses when approximately the same electrical charge was provided to the animal. The results indicate that for stimulation (at least concerning this particular approach to measurement) nanosecond pulses require higher energies than TASER pulses to obtain the same result. An important contribution of these efforts to the study of nanosecond pulse effects was the design and implementation of an appropriate testing system for animal studies.

Example 3

Incapacitation Studies

The goal of incapacitation is to prevent voluntary movement, whereas the endpoint in the above-described experiments was triggering the involuntary local movement of a muscle. A muscular disruption device is not concerned with causing a twitch (action) but instead the major concern is in preventing an action. Although these processes are somewhat related and involve neuromuscular excitation, the underlying physiological mechanisms may be substantially different.

In the whole animal, the threshold involuntary twitch is most likely evoked via a reflex pathway, by stimulation of peripheral receptors in the immediate vicinity of the stimulation electrode. It is unlikely that even a very strong, but local stimulation can produce the expected incapacitation effect. Instead, the incapacitation requires excitation/contraction of remote muscles, so that no voluntary movement could be performed. A stimulus that can be very good for local excitation (a pinch, for example) may do little or nothing to excite remote muscles to the point of incapacitation. This is the case for electrical stimuli as well: if an electrical stimulus is more effective at producing a threshold response by a reflex pathway, it does not automatically mean that the same stimulus is better for incapacitation.

Therefore, the ability of an electric stimulus to evoke local threshold responses is not necessarily indicative of the efficiency of this stimulus to cause incapacitation (although some correlation may take place, the data will be inconclusive). Hence, instead of studying threshold responses, a different method for more direct evaluation and comparison of the incapacitation efficiency of TASER and ns pulses was utilized. In an animal model (rat), voluntary movement were motivated by low-current electrical stimuli delivered directly to the sensorimotor cortex. Next, a comparison was made of how application of TASER and nanosecond pulses interfere with the animal's ability to perform movements initiated by cortical stimulation.

Methods: The experiments were performed in male Sprague-Dawley rats (Charles River Laboratories) weighing 250-400 g. Under mixed ketamine (80 mg/kg i.p.) and xylazine (12 mg/kg i.p.) anesthesia, the animal was fixed in a stereotaxic frame. Temperature was maintained at 33-37° C. (rectal) using a heated water blanket and an overhead heater lamp. The scalp was removed to expose the cranium, and its surface was cleaned and dried. The head position in the rostrocaudal plane was adjusted to level bregma and lambda skull landmarks. Two burr holes were made over the left hemisphere above the left hind paw motor cortex, 1.5 mm posterior and 1.5 mm and 3.5 mm lateral to bregma in the left hemisphere. These coordinates were selected to provide the maximum coverage of the cortical motor zone that elicits movements of the contralateral (right) hind paw. The dura was pierced and two separate stimulating electrodes (made of 0.25-mm diameter tungsten wire with no electrical insulation) were inserted to the depth of 1.5 mm below the pia. For the hind limb region, this depth corresponds to the minimum stimulation threshold and is still above the white matter. Relative to bregma, the medial electrode was deepened by about 2 mm and the lateral one by about 2.6 mm (G. Paxinos and C. Watson. The rat brain in stereotaxic coordinates, Academic Press (1998)).

The electrodes were glued to the skull; the animal was released from the stereotaxic frame and placed into a hammock with through-holes for hind limbs. The right hind limb was connected to an isotonic force transducer plugged into a BIOPAC data acquisition system (World Precision Instruments, Sarasota, Fla.). The electrodes for high-voltage (HV) stimulation (either Taser or nanosecond pulses) were affixed to the left hind paw and to right back side of the body. Contrary to the stimulation experiment (infra), the electrodes were not penetrating the skin of the animal. Implanted cortical electrodes were connected to the output of two paired Grass 88 stimulators (Astro-Med, West Warwick, R.I.) via an optical insulation unit (Astro-Med).

Cortex stimulation (CS) paradigm was similar to the one proposed earlier (V. C. Austin et al. *Magn Reson Med* 49(5): 838-47 (2003); V. C Austin et al. *Neuroimage* 24(1): 92-100 (2005)). Rectangular pulses of 0.3-0.6 ms duration, 0.5-2 mA were applied at 200-300 Hz in 50 ms trains repeated four times with 500-ms intervals. This stimulation, which elicited four distinct twitches of the contralateral hind paw, was repeated once every 10 sec. Data acquisition by the BIOPAC was triggered by the first stimulus in each train and continued for 4 sec. Following a 6-sec no-recording interval, the acquisition was triggered again by the next CS train, and the new record was appended at the end of the previous one, and so forth.

On demand, the Grass stimulators also triggered an HV pulse, with a delay of 900-950 ms after the CS train onset. This delay was chosen so that the HV pulse arrived shortly before the 3rd CS stimulus in each train. Therefore, one of the principal endpoints in this study was the change in the third twitch by the preceding HV stimulus, as compared to the CS trains without HV stimulation.

All experiments began with several CS trains. Upon reaching a stable twitch response to the CS, a single HV pulse was delivered concurrently with the next CS train. Afterward, the CS trains were either delivered uninterruptedly and unchanged for an extended period of time (to detect delayed effects of HV, such as delayed twitch inhibition, see "Results"), or were temporarily turned off to deliver a single HV pulse without concurrent CS stimulation. The trace with the HV-induced twitch was subtracted from the trace with the CS+HV-induced twitch, to reveal the true amplitude of the CS-induced twitch when it was preceded by the HV stimulus (see FIGS. 5A and 5B). This amplitude was compared to the amplitude of CS-induced twitches in a train prior to the HV stimulation, to establish the HV-induced inhibition or facilitation of CS-induced twitches. The experiments with different types and voltages of HV pulses continued for 2-5 hours. Animals were given additional shots of anesthetics when necessary.

Results: Originally, it was expected that HV pulses should cause immediate inhibition of CS-induced twitches, proportionally to HV peak voltage and current, and/or to the pulse energy. However, the experiments established complex responses to HV pulses, which might include immediate inhibition, immediate facilitation, and a long-lasting delayed inhibition of CS-induced hind limb twitches.

Figure 5A:
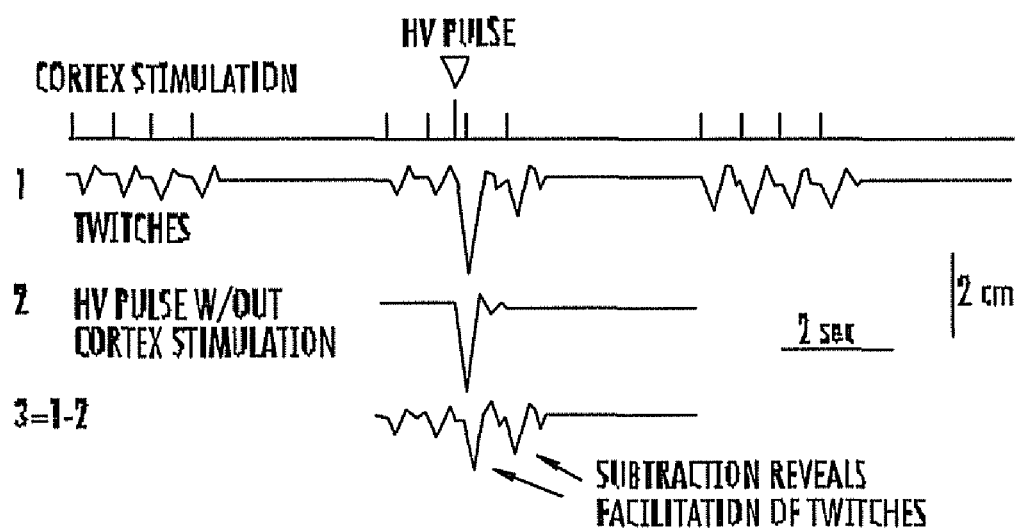
FIGS. 5A and 5B are traces showing immediate facilitation (FIG. 5A) and inhibition (FIG. 5B) of hind limb twitches by a high-voltage (HV) pulse.
Figure 5B:
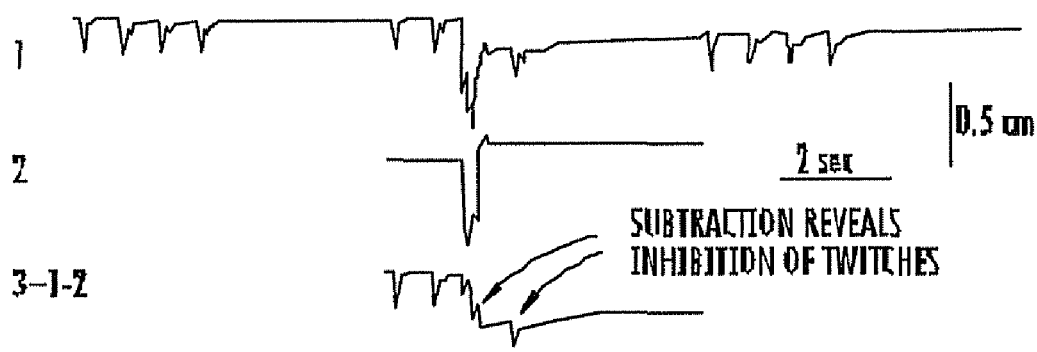
Figure 6A:
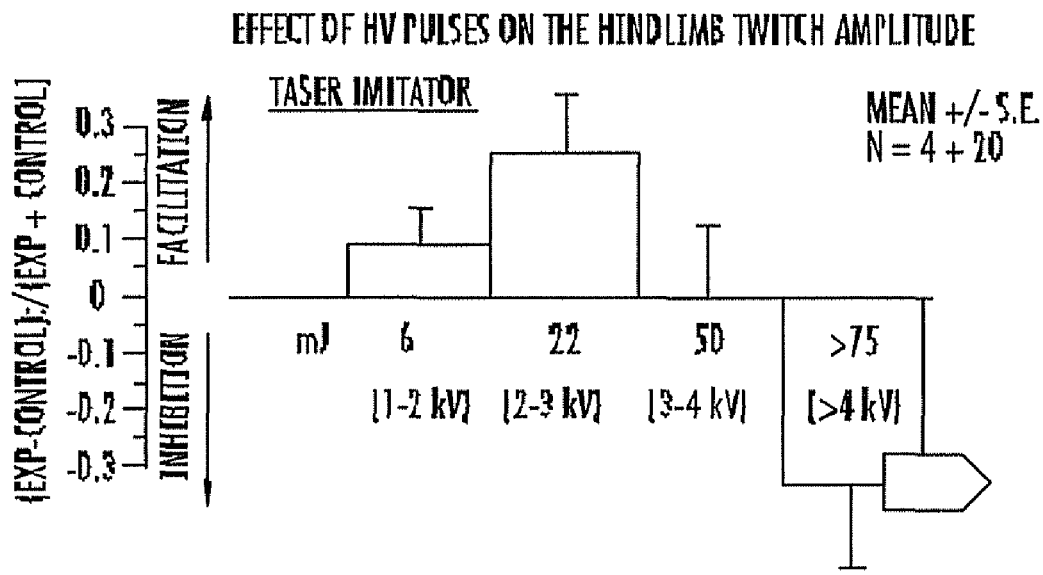
FIGS. 6A and 6B are graphs showing the effect of high voltage pulses on the amplitude of the twitch which followed immediately after the exposure to a HV pulse (FIG. 6A-TASER pulses). Results from nanosecond pulses are shown in FIG. 6B.
Figure 6B:
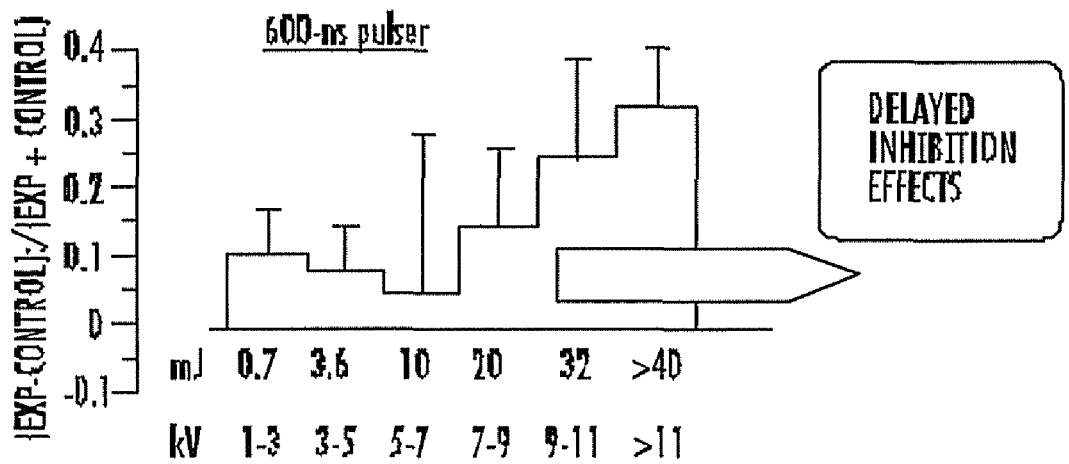
Figure 7A:
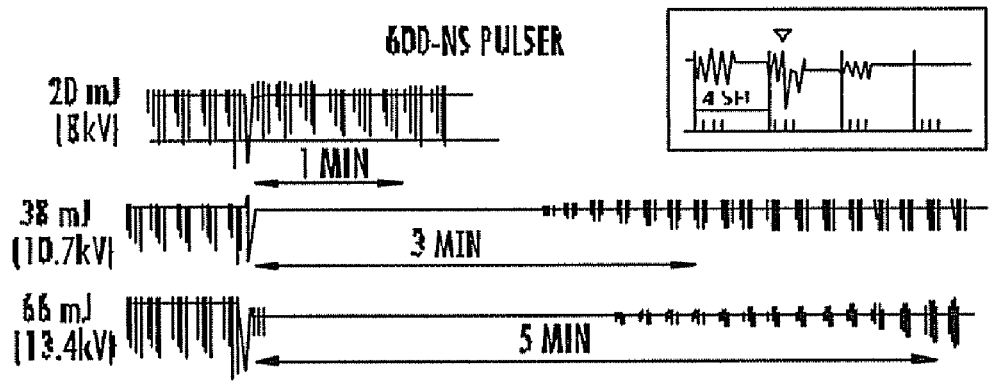
FIGS. 7A and 7B are traces showing the results of muscular disruption studies—effects of HV pulses on the hindlimb switch amplitude (FIG. 7A 600 ns pulser.
Figure 7B:
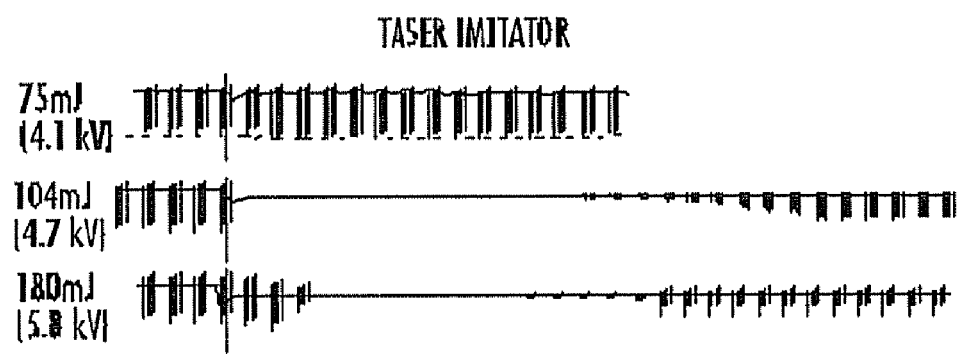
Figure 8A:
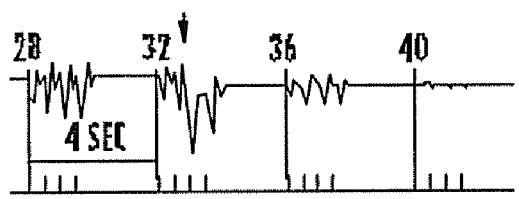
FIGS. 8A-8C are traces showing the induction of prolonged incapacitation by a single high-voltage 600-ns pulse.
Figure 8B:
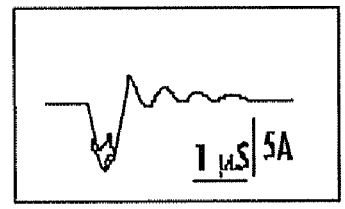
Figure 8B:
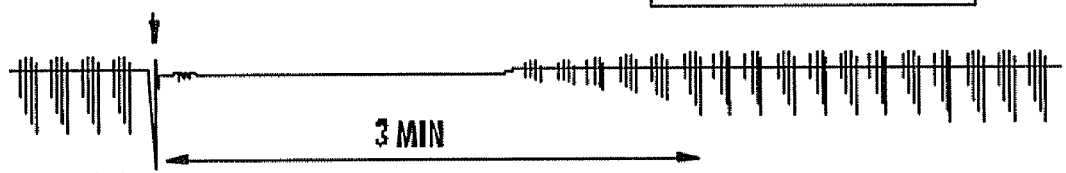
Figure 8C:
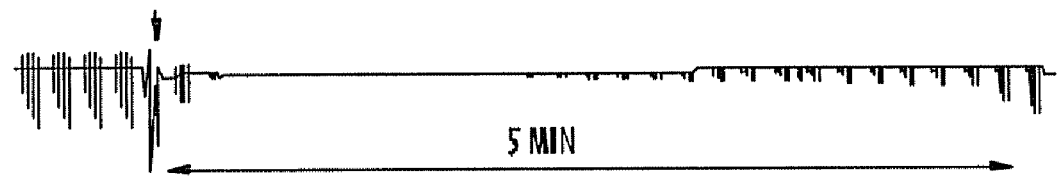

Immediate Effects: Immediate twitch facilitation, as shown in FIG. 5A, is the most typical response to nanosecond pulse stimulation in a wide range of peak voltage (1.3-16 kV) and pulse energy (0.3-103 mJ). In almost half of the experiments, the ns pulse increased the amplitude of CS-induced twitches by more than 50%, and in isolated experiments a 2-3-fold increase was observed. The magnitude of this effect increased linearly with increasing the peak voltage from 5-7 to 9-11 kV and higher (FIG. 6B, lower trace).

It is noted that ns pulses can sometimes cause profound immediate facilitation of twitches at voltages so low that the ns pulse itself (i.e., not accompanied by the CS stimulation) produced no twitch at all. The data indicate that ns pulses can increase the excitability of neurons in the efferent pathway without eliciting a motor response. The ability of nanosecond pulses to facilitate neuromuscular responses can be employed in treatment of neuromuscular diseases and conditions associated with decreased excitability in the efferent pathway from cerebral neurons to peripheral muscles.

One might assume that facilitated response to HV+CS stimulation was not because of HV-induced facilitation, but instead it was the increased response to the HV pulse when it was delivered after two first stimuli in the CS train. To check this possibility, there were employed 2-stimuli CS trains, and the HV pulse was delivered with the same delay after the train onset. In these experiments, the HV-induced twitch was not facilitated, as compared to the situation when HV stimulation was not accompanied by any CS stimuli. Hence, the facilitation of the third twitch described above was the true effect of the preceding HV stimulation.

The immediate effects of Taser pulses were substantially different. At low peak voltages (2-3 kV), the predominant effect was facilitation of CS-induced twitches; at higher voltages of 3-4 kV, the effects were variable, and at voltages over 4 kV the predominant effect was twitch inhibition (FIG. 6A).

Delayed Inhibition: Perhaps the most interesting phenomenon repeatedly observed at relatively high pulse voltages (energies) was a long-lasting delayed inhibition of CS-induced twitches. Examples for this effect are shown in FIGS. 7A, 7B and 8A-8C. After a five to twenty second delay after HV application, nanosecond pulses, and at higher energies also TASER pulses, cause a long lasting inhibition and incapacitation of the animal. The time of this incapacitation, which in the range of the observations lasted up to 15 minutes, appears to depend strongly on the voltage amplitude or the electrical energy, respectively. This effect appears not to have been obtained in earlier studies.

The delayed inhibition of twitches is a manifestation of prolonged disruption of neuromuscular functions by a single HV pulse, or a sequence of several high voltage pulses, and therefore is of particular interest for applications that are intended to cause temporary incapacitation. Typically, delayed inhibition developed within 10-20 sec after a HV pulse, and lasted from tens of seconds to over 10 min, proportional to the pulse voltage and energy. The delayed inhibition could be evoked by either TASER or nanosecond pulses, but the energy expenditure to induce it was 2-3-fold less when using ns pulses (FIGS. 6A, 6B).

The experiments described above employed a new methodology of assessment of incapacitation induced by HV pulses. Indeed, the pathway from the sensorimotor cortex down to spinal motoneurons and further to effector muscles is the same pathway that is involved in voluntary movements. Hence, blockage of this pathway, one way or another, is equivalent to the blockage of voluntary movements, or incapacitation. This new methodology proved to be a useful tool to explore incapacitation effects of TASER and nanosecond pulses.

Different HV effects observed demonstrate the complexity of the whole organism response to this stimulus. The enhancement of CS-induced twitches by HV pulses indicates temporary hyperexcitability in the efferent motor pathways. The implications of this change for incapacitation techniques remain unclear; however, one may speculate that hyperexcitability might interfere with coordination of voluntary movements, ultimately making any coordinated movement impossible. The immediate inhibition of twitches, on the other hand, demonstrates that following a strong enough HV stimulus, the downstream conduction in the efferent motor pathway is suppressed; that is, the animal is temporary incapacitated. The same interpretation applies to the discovered phenomenon of delayed inhibition, which potentially may be employed for development of a new generation of low-energy output incapacitation devices.

The mechanisms underlying delayed inhibition have not been understood. It is hypothesized by the present inventors that it is caused by a long lasting inhibition of spinal motor neurons; however, other possibilities and confounding factors have not been excluded and need to be explored in more detail. Such confounding factors are, for example, HV pulse effects on the depth of animal anesthesia (CS reliably induces leg twitches only within a certain "window" of the anesthesia depth), or the electrical pick-up of the HV pulse by CS electrodes and potential damage to cortex by resulting pulse of current. The latter artifact seems unlikely because an optical stimulus isolation unit was used in all experiments; nonetheless, in future experiments, it will be advantageous to employ transcranial magnetic stimulation (TMS) instead of direct electrical stimulation of cortex by implanted electrodes.

Shortening the pulses into the subnanoseond range (which would allow the use of ultrawideband antennas for the delivery of electric field pulses into a target) may also improve the efficiency of the pulses further.

In order to delivery the electrical energy to a mammal without using cables a pulse generator could be used to charge a capacitor to the desired voltage. The two poles of the capacitor would be connected to two electrodes. Instead of connecting target and pulse generator by means of cables, the charged capacitor could transfer the electrical energy to the target.

Example 4

Membrane Permeabilization and Cell Damage by Exposure to Ultra-Short Electric Field Pulses In this study, a broad, first step analysis of the nature of nsPEF-opened CPs and their possible connection to cell damage was conducted. For the first time, some properties of the CPs were described, their partial blockers identified, and clear correlation established between the membrane permeabilization and the severity of cell to necrotic damage in nsPEF-exposed cells.

Materials and Methods

Cell cultures: Experiments were performed in GH3 cells (a murine pituitary cell line) and HeLa cells (human epithelial cancer), both obtained from American Type Culture Collection (ATCC, Manassas, Va.) and cultured according to their recommendations. Cells were grown in 75-cm² flasks at 37° C. with 5% $CO_2$ in air. GH3 cells were cultured in Ham's F12K medium supplemented with 2.5% fetal bovine serum (FBS) and 15% horse serum (Atlanta Biologicals, Norcross, Ga.). HeLa cells were propagated in Eagle minimum essential medium with 10% FBS. The cultures also contained 1% L-glutamine and 1% penicillin/streptomycin (Mediatech Cellgro, Herndon, Va.). For passaging, cells were removed from the substrate with 2-3 ml of 0.25% Trypsin with 2.21 mM EGTA. The cultures were maintained in the logarithmic stage of growth and used at passages 3-15. For a passage immediately preceding the experiments, cells were grown attached to 8- or 10-mm diameter glass cover slips in 35-mm Petri dishes. The cover slips were pretreated with poly-l-lysine (Sigma-Aldrich, St. Louis, Mo.) to improve cell adherence.

Chemicals and solutions: The names and ionic compositions of pipette/bath solution pairs used in this study are given in Table 1. These pairs were formulated to explore, in the first approximation, how different ion substitutions would affect Gm and the reversal potential (Erev) after nsPEF exposure. Two pairs (Cs/Na and Cs/Ba-TEA) were also used to explore nsPEF effects on voltage-gated $Na^+$ and $Ca^{2+}$ channels, respectively. In general, solution pairs from the top to the bottom of the Table 1 contain diminishing amounts and variety of monovalent ions, i.e., K and/or Na were replaced with larger $Cs^+$, $TEA^+$, or $NMDG^+$. The contents of anions ($Cl^-$ and $HEPES^-$) were kept almost constant and the same in bath and pipette solutions, except for the last pair, where most of the pipette $Cl^-$ was replaced with $HEPES^-$. The pH of pipette and bath solutions was adjusted to 7.4 and 7.2, respectively; the ionic contents shown in Table 1 already include any extra amounts of ions added as a base or acid for pH adjustment. The osmolality of all solutions was between 290 and 320 mOsm, as measured with a freezing point microosmometer (Advanced Instruments, Inc., Norwood, Mass., USA). When lanthanide salts were added to the bath solution of the K/Na combination as a cocktail (1 mM $GdCl_3$ + 1 mM $LaCl_3$), the content of NaCl was appropriately reduced to maintain the osmolality constant.

All chemicals were purchased from Sigma-Aldrich, except tetrodotoxin, which was received from Alomone Labs (Jerusalem, Israel).

Patch clamp recording: Cells on a cover slip were transferred into a glass-bottomed chamber (Warner Instruments, Hamden, Conn.) mounted on a motorized stage (Prior Scientific Inc., Rockland, Mass.) of an IX71 FluoView™ 300 confocal laser scanning microscope. Recording pipettes were pulled from 1B150F-4 glass (World Precision Instruments, Sarasota, Fla.) to a tip resistance of 1.5-3 MOhm and moved into a position with a model 6500 hydraulic micromanipulator (Siskiyou, Grants Pass, Oreg.). Electrophysiology data were acquired using a Multiclamp 700B amplifier, Digidata 1322A A-D converter, and pCLAMP 10 software (Molecular Devices, Foster City, Calif.). The analog signal was low-pass filtered at 2 or 5 kHz, and digitized at "oversampling" rates of 10 to 50 kHz. The series resistance was not compensated. Typical values of the seal and access resistance were 4-15 GOhm and 4-10 MOhm, respectively, except for a solution pair HEPES/Cl. Greatly reduced contents of small, high-mobility ions in the pipette solution of this pair resulted in a high access resistance of 50-70 MOhm. The data from these experiments were analyzed differently (see below).

As shown in the inventors preliminary experiments, nsPEF exposure could be damaging to the gigaohmic seal between the cell membrane and the glass pipette, thereby effectively destroying the patch-clamp recording configuration. Hence, all cells in this study were exposed intact, and only after the exposure the glass pipette was brought in contact with the cell membrane. The exposure of intact (rather than already "patched") cells effectively removed any concerns about possible artifacts caused by the presence of the glass pipette during the exposure.

Once the whole-cell configuration was formed, the membrane resistance and capacitance (Rm and Cm) were measured using the Membrane Test utility of pClamp10 software. The holding level was set at −70 or −60 mV; 10- or 20-mV test pulses were applied at 30- to 100-Hz rates and averaged on-line (n=6-12). The membrane potential (MP) was measured by switching briefly from voltage to current clamp mode at I=0.

After Cm compensation, the holding membrane potential was set to −70 mV. In most experiments, the I-V relationship was obtained by applying voltage ramps, typically from −100 to +100 mV within 20-40 ms, and preceded by a brief step to −100 mV. Passive Gm was determined as the slope of the I-V curve by a best fit linear approximation through a region that contained no visible voltage-gated currents, usually from −80 to −50 mV. As one would expect, these Gm values correlated very closely with the inverse of Rm values measured using the Membrane Test. Erev was determined in a usual manner, as an intercept of the best fit line with abscissa.

Cm could not be reliably compensated in experiments when the access resistance was high (with NMDG-HEPES pipette solution). Therefore, whole-cell currents elicited by the voltage ramps could be distorted in an unpredictable manner by the presence of the capacitive component. For more accurate measurements, a voltage step protocol was used by the inventors instead of ramps; the whole-cell current was measured at −70 mV (holding) and upon reaching the steady-state level after the voltage was stepped to −80 and −100 mV. Gm and Erev were measured from a straight line drown through the three data points.

All voltages values reported below in this paper and shown on the graphs were corrected for respective junction potentials.

Exposure to nsPEF and local E-field modeling: A Blumlein line pulse generator (Kolb, J. F., S. Kono, and K. H. Schoenbach. 2006. Nanosecond pulsed electric field generators for the study of subcellular effects. *Bioelectromagnetics* 27:172-187) produced nearly rectangular 60-ns pulses that were delivered to the selected cell by a pair of tungsten electrodes (0.125 mm electrode diameter, 0.31 mm gap between the electrodes). With a help of a micromanipulator, the electrodes were positioned 5-10 μm above the surface of the cover slip on the sides of the selected cell; the cell was in the middle of the gap between the electrodes, at a distance of about 50-100 μm from their tips.

The E-field between the electrodes was determined by 2D and 3D simulations with the finite element Maxwell equations solvers EStat and Amaze-3D, respectively (both by Field Precision, Albuquerque, N. Mex.), both yielding similar results. At the location of the cell, the E-field was about 12 kV/cm for the pulse amplitudes of 540-580 V used throughout this study. The respective energy deposition density was 85 mJ/cm3, corresponding to the maximum (adiabatic) local heating of 0.02° C. per pulse. Small inaccuracies in positioning of the electrodes, e.g., by 50-70 μm, had no appreciable effect on the E-field delivered to the cell. For multiple pulse exposure, electric field pulses were triggered manually at a rate of about 1.5 pulses/sec.

To ensure that nsPEF treatment is the only difference between the exposed and control cells, sham exposures were always run in parallel, in the same cell populations, and were alternated in a random manner with actual exposures. For a sham exposure, all procedures and protocols were identical, but no pulses were triggered.

Results

Ionic permeability of nsPEF-opened conductance pores: The effect of ionic composition of extra- and intracellular solutions on Gm in nsPEF-exposed cells. A whole-cell configuration was established in 70-110 sec after exposure to a brief nsPEF train (5 pulses), or after a sham exposure (control), and the I-V relationship was measured by applying a voltage ramp within the next 40-50 sec. NsPEF exposure increased Gm to about 3-4 mS, which was 10-30 times higher than in parallel control cells. Post-exposure Gm was remarkably similar in all exposed groups, apparently unaffected by such solution manipulations as removal of external $Ca^{2+}$ and addition of EGTA, replacement of $K^+$ with $Cs^+$ and addition of 20 mM $TEA^+$, or replacement of both $Na^+$ and $K^+$ with $Cs^+$ and $TEA^+$ and addition of 10 mM $Ba^{2+}$.

Post-exposure Gm was just marginally lower in symmetrical solutions where both $Na^+$ and $K^+$ were replaced with a larger $NMDG^+$ cation. These data suggested that nsPEF-opened CPs were permeable to various small ions and showed little ability to discriminate between them.

control cells plus 0.18 mS added by exposure). Actually measured Gm was an order of magnitude greater (3.2 mS), which could occur only by a concurrent increase in Cl- and cationic conductance(s).

Gm recovery took place in a cell already dialyzed by the pipette solution; neither bath nor pipette solutions contained any ATP or glucose, and the ionic milieu was far from physiological conditions. This observation shows that sealing of nsPEF-opened pores is probably a passive physico-chemical process that occurs independently of the energy supply and is not actively controlled by the cell.

Overall, such properties as permeability to both small cations and anions, with little or no selectivity between them, and gradual "passive" resealing are consistent with the expected behavior of nano-electropores, which are understood as temporary defects (or holes of certain size) in the lipid bilayer. However, the lifetime in the range of minutes is rather unexpected from such small membrane defects. At present, possible activation of some endogenous ion channels by nsPEF cannot be ruled out and remains an alternative explanation for the long-lasting Gm increase after the exposure.

TABLE 1

Ionic contents of pipette/bath solution combinations

| Name (pipette/bath) | $Na^+$ | $K^+$ | $Ca^{2+}$ | $Mg^{2+}$ | $Cs^+$ | $TEA^+$ | $NMDG^+$ | $Cl^-$ | $HEPES^-$ | $EGTA^-$ | Glucose |
|---|---|---|---|---|---|---|---|---|---|---|---|
| K/Na—Ca | 10/140 | 140/5 | 0/2 | 1/2 | — | — | — | 152/158 | 10/10 | — | 0/10 |
| K/Na | 5/140 | 140/5 | 1/0 | 1/4 | — | — | — | 149/153 | 10/10 | 10/0 | 0/10 |
| Cs/Na | 5/120 | — | 1/0 | 1/4 | 130/6 | 20/20 | — | 149/153 | 10/10 | 10/1 | 0/10 |
| Cs/Ba-TEA* | — | — | 0/10 | 4/2 | 120/0 | 20/134 | — | 140/154 | 10/10 | 10/0 | 0/10 |
| NMDG/NMDG | — | — | 2/2 | 2/2 | 10/10 | — | 140/140 | 140/140 | 10/10 | — | — |
| HEPES/Cl | — | — | 0/2 | 1/2 | 10/10 | — | 68/140 | 29/140 | 129/10 | 1.3/0 | — |

*$Ba^{2+}$ was used instead of $Ca^{2+}$; the bath solution also contained 0.001 mM of tetrodotoxin.
All ion concentrations are in mM. Abbreviations; HEPES, 4-(2-Hydroxyethyl)piperazine-1-ethanesulfonic acid; TEA, Tetraethylammonium; EGTA, Ethylene glycol-bis(2-aminoethylether)-N,N,N',N'-tetraacetic acid; NMDG, N-methyl-D-glucamine.

CPs' properties were further explored using solutions asymmetrical on anions ($Cl^-$ and $HEPES^-$), while most of small cations were replaced with $NMDG^+$. These solutions were formulated to spread the individual reversal potentials (Nernst equilibrium) for the major ions present as far apart as possible: Erev was negative at −40 mV for $Cl^-$, but positive at +18 mV for $NMDG^+$ and at +63 mV for $HEPES^-$.

Gm in control cells was very low (about 0.1 mS, n=5) and Erev was close to that of $Cl^-$. NsPEF increased Gm greatly, to 2.8-3 mS in 4 cells and to 10 mS in one cell. Erev in 4 out of 5 exposed cells remained at about −40 mV, which can only be explained by a profound increase in Cl_ permeability ($P_{Cl}$), with little or no change in $P_{NMDG}$ or $P_{HEPES}$. In one cell, however, Erev was close to zero, which was indicative of a concurrent increase of $P_{NMDG}$ and/or $P_{HEPES}$. Interestingly, Erev in this cell returned to about −40 mV by 3 min after nsPEF exposure and stayed at this value while Gm gradually recovered over the next 10 min.

Fitting the experimental data into Goldman-Hodgkin-Katz equation shows that the sole increase in $Cl^-$ permeability cannot explain the 10-fold or greater increase in Gm in exposed cells. For example, the change in Erev from −60 mV (control) to −15 mV (exposed) would correspond to the additional $Cl^-$ conductance of only about 0.18 mS (if GCl in control cells is assumed negligible and ionic conductances are considered proportional to ionic permeabilities). In this example, the selective increase in PCl by nsPEF would result in Gm of about only 0.4 mS (0.21 mS originally present in Comparative effects of nsPEF on membrane permeabilization in GH3 and HeLa cells: In preliminary experiments, it was found by the inventors that nsPEF effectively permeabilized plasma membrane in GH3, PC12, and Jurkat cells, but not in HeLa cells. This finding could provide important keys to understanding the nature of nsPEF-induced membrane permeability. For example, HeLa cells have less endogenous ionic current and seem to have no voltage-gated ion channels. If nsPEF induced permeability indeed results from opening of some naturally present ion channels (rather than from de novo formation of electropores), than HeLa cells could be insensitive to nsPEF simply because they lack the vulnerable type of endogenously expressed ion channels. Should it be the case, then even very long nsPEF trains will produce no long-lasting permeabilization in HeLa cells.

Since HeLa cells are much larger (Cm=25±3 pF vs 5.8±0.6 pF in GH3), for adequate comparison all current and conductance values are normalized to Cm. Without exposure, normalized Gm was very similar at 0.04-0.05 mS/pF in both cell lines. In GH3 cells, 1 and 5 pulses increased this value to 0.1 and 0.54 mS/pF, respectively, and 10 or 20 pulses caused so severe damage that patch clamp measurements could no longer be reliably performed. In contrast, Gm in HeLa cells was only marginally increased by 5 pulses and still remained well within measurable limits even after 20 pulses (0.07 and 0.14 mS/pF, respectively).

Hence, the experiments established that it was possible to produce the membrane permeabilization in HeLa, although it took many more pulses than for GH3 cells. This result did not provide a clear answer to the above question if nsPEF-opened CPs are de novo electropores or some endogenous ion channels, as the latter possibility was not ruled out. One can speculate, for example, that increased Gm was caused by opening of endogenous ion channels both in GH3 and HeLa, but in HeLa they were expressed in smaller quantities leading to decreased nsPEF sensitivity. No matter what is the exact reason for vastly diminished Gm change by nsPEF in HeLa compared to GH3, further comparison involving other nsPEF effects (e.g., cell death, morphological changes) in these two cells lines appears useful to establish possible connection between membrane permeabilization and other nsPEF effects.

Cytophysiological effects of nsPEF trains: The absence or low uptake rates of membrane-impermeable dyes PI (FW 668) and TB (FW 961) by nsPEF-exposed cells were often used as an argument that nsPEF effects are primarily intracellular. Still other isolated studies were able to detect increased PI uptake, although only in a low-conductance medium and using high E-field intensities, or only following very long nsPEF trains. The inventors' patch-clamp data indicated that PI or TB uptake by the cells exposed to 12 kV/cm, 60-ns pulses is unlikely, as the conductance pores typically showed little or no permeability even to much smaller ions NMDG$^+$ (FW 195) and HEPES$^-$ (FW 238).

Indeed, nsPEF exposure in the presence of 10 mg/ml of PI in the medium did not cause any dye uptake by either GH3 or HeLa cells. Moreover, the cells remained impermeable to PI even after extra-long trains of 200 pulses, which caused necrotic changes in cells morphology, and even when the observation period was extended to 30-60 min after the exposure. As a positive control, the same cells were permeabilized with 0.03% of digitonin and displayed bright PI fluorescence in 1-2 min after addition of the drug into the bath.

In GH3 cells, the first necrotic manifestations could be seen shortly (within 20-30 sec) after the onset of nsPEF pulsing. As the train proceeded and after the exposure, the cells developed severe swelling, membrane blebbing, and cytoplasm granulation; these changes only became more severe with time and showed no decline. The necrotic manifestations were notably weaker in HeLa cells: the only visible effect during and immediately after the exposure was cytoplasm granulation, and isolated cells also might develop small blebs at 15-30 min after the treatment. These data pointed to a possible connection between the extent of plasma membrane permeabilization and overall cell damage by nsPEF.

Cell swelling and CPs opening: Despite a likely connection between the morphological changes and the increase of whole-cell conductance, the causal relation between these two effects remains unclear. Cell stretching and swelling can activate nonselective cation channels (NSCCs), some of which have been identified as members of the transient receptor potential (TRP) channels family. Volume regulation triggered by osmotic swelling may include activation of volume sensitive Cl$^-$ channels. Conversely, blockage of TRP channels by ruthenium red (1 μM) or by lanthanide ions (La$^{3+}$ and Gd$^{3+}$, 100 μM) reduced swelling and other deleterious effects of oxygen-glucose deprivation in hippocampal CA1 neurons, implicating that TRP channels activation may by itself be the mechanism that leads to cell swelling. Similarly, Na$^+$ influx through oxidative stress-activated NSCCs was shown to be the cause of swelling and necrotic death in liver cells; addition of Gd$^{3+}$ sharply decreased the number of necrotic cells. NSCCs and Cl$^-$ channels are naturally expressed in HeLa and GH3 cells, so their activation could explain, at least to some extent, the nsPEF effects described above.

To check if activation of endogenous NSCCs was responsible (at least in part) for observed nsPEF effects, an attempt was made by the inventors to modify these effects with ruthenium red and with lanthanide ions. It should be noted, however, that these substances are not truly specific and can affects various other channels and intracellular processes.

Ruthenium red was added to the bath solution of the K/Na pair (see Table 1) at 10, 50, or 200 μM prior to exposure to 1 or 5 pulses, and the whole-cell currents were recorded after the exposure in the usual manner. Surprisingly, the presence of 50 and 200 μM of ruthenium red worsened the condition of nsPEF-exposed cells while having no apparent effect on the control ones. Exposed cells displayed very low input resistance and fast rundown, to such extent that no meaningful patch-clamp measurements could be performed. At a lower concentration of 10 μM (which is still 10-fold higher than used earlier to prevent cell swelling), the presence of ruthenium red neither enhanced nor inhibited the membrane conductance increase by nsPEF.

In contrast, the addition of 1 mM of Gd$^{3+}$ or of a 1 mM Gd$^{3+}$+1 mM La$^{3+}$ cocktail to the bath prior to exposure strongly and consistently attenuated the effect of nsPEF both in K/Na and in Cs/Na solutions. Furthermore, adding 1 mM Gd$^{3+}$ to cells already permeabilized by nsPEF almost instantly restored their membrane resistance. The restored Rm in all cases still remained below its value in control cells, despite rather high concentrations of the lanthanides. Concentration dependence of the protective effect of the lanthanides has not been explored in detail yet; however, initial trials showed no protection at a still high Gd$^{3+}$ concentration of 0.2 mM.

The presence of 1 mM Gd$^{3+}$+1 mM La$^{3+}$ cocktail in the bath also prevented or markedly attenuated the necrotic manifestations during and after exposure to long nsPEF trains. This finding not only clearly related the necrotic morphological changes to the plasma membrane permeabilization, but also showed that permeabilization was the cause of cell swelling (and not vice versa).

We claim:

1. A method of incapacitating an animal or a person, said method comprising:
   generating a plurality of electric pulses using a pulse generator, each of the plurality of pulses having a pulse duration less than 10 microseconds and configured to deliver a pulse energy less than 103 mJ; and
   subjecting the cells or tissues of the animal or person to an electric field generated by the plurality of pulses to incapacitate the animal or person.

2. The method of claim 1, wherein the generating further comprises configuring the plurality of pulses to deliver a pulse energy from about 0.3 mJ to about 103 mJ.

3. The method of claim 2, wherein the further comprising configuring the plurality of pulses to deliver a pulse energy from about 38 mJ to about 66 mJ.

4. The method of claim 1, wherein the generating further comprises configuring the plurality of pulses to have a pulse duration from about 300 nanoseconds to about 600 nanoseconds.

5. A method of facilitating neuromuscular responses in treatment of neuromuscular diseases and conditions associated with decreased excitability in the efferent pathway from cerebral neurons to peripheral muscles comprising:
   providing a pulse generator comprising a capacitor or pulse network configured for generating a plurality of electric pulses having a pulse duration less than 10 microseconds; and applying the pulse generator to a tissue to be treated via two contacts so as to generate electric fields up to 500 kV/cm in the portions of the tissue between the two contacts.

6. A method of blocking nerve conduction comprising:
providing a pulse generator comprising a capacitor or pulse network configured for generating a plurality of electric pulses having a pulse duration less than 10 microseconds; and
applying the pulse generator to a tissue including a nerve to be blocked via two contacts so as to generate electric fields up to 500 kV/cm in the tissue between the two contacts;
permeabilizing the membrane by decreasing local input resistance using the electric field; and,
blocking nerve conduction in the nerve.

7. A method of blocking nerve conduction comprising:
providing a pulse generator comprising a capacitor or pulse network configured for generating a plurality of electric pulses having a pulse duration less than 10 microseconds; and
applying the pulse generator to tissue including a nerve to be blocked via two contacts so as to generate electric fields up to 500 kV/cm in the tissue between the two contacts;
disrupting ion channels and inhibiting the ion channels using the electric field; and,
blocking nerve conduction in the nerve.

8. The method of claim 7, wherein the ion channel is a voltage gated Na+ channel.

* * * * *